United States Patent [19]

Kasdan

[11] Patent Number: 4,864,593
[45] Date of Patent: Sep. 5, 1989

[54] METHOD OF MEASURING PLASMA DENSITIES AND TEMPERATURES

[75] Inventor: Abraham Kasdan, Englewood Cliffs, N.J.

[73] Assignee: North American Philips Corporation, New York, N.Y.

[21] Appl. No.: 125,024

[22] Filed: Nov. 24, 1987

[51] Int. Cl.⁴ .............................................. G01N 23/04
[52] U.S. Cl. ........................................ 378/4; 378/54
[58] Field of Search .................... 378/4, 17, 6, 901, 54

[56] References Cited

FOREIGN PATENT DOCUMENTS 0175553 8/1986 Japan ........................................ 378/4

Primary Examiner—Carolyn E. Fields
Assistant Examiner—Joseph A. Hynds
Attorney, Agent, or Firm—Jack E. Haken

[57] ABSTRACT

An X-ray computed tomography (CT) scanner is used to measure the density of mercury plasma in an operating arc lamp.

12 Claims, 2 Drawing Sheets

METHOD OF MEASURING PLASMA DENSITIES AND TEMPERATURES

BACKGROUND OF THE INVENTION

This invention relates to a method for the determination of the density distribution of gas phase constituents in a plasma. The term "plasma" as employed in the instant application means an ionized gas which contains equal numbers of ions and electrons.

In particular the invention relates to a method for the determination of the density distribution of gas phase constituents of a plasma existing in an operating discharge lamp.

The method of the invention is particularly useful for the determination of the density distribution of mercury ($H_3$) present in the plasma of an operating high pressure metal vapor discharge lamp.

The determination of the density distribution of the gas phase species in a plasma is important in understanding the chemistry of the plasma and thereby enhances the ability to improve the quality of the plasma.

Also, in many types of plasmas present in high density discharge lamps, the temperature distribution in such plasmas may be readily determined from its density distribution by the use of the gas laws. Knowledge of the temperature distribution in a plasma is also highly useful in understanding the chemistry of the plasma.

The density distribution of species in the plasma existing in an operating discharge lamp particularly a high pressure metal vapor discharge lamp, affects its efficacy, color rendition and useful life.

Thus, knowledge of the density distribution of the species present in a discharge lamp plasma is a key to the optimization of the design of the lamp. Additionally, the temperature distribution of the plasma which critically affects the operation of the lamp, may also readily be determined from the density distribution by employing the gas laws.

Attempts have been made to measure the temperature distribution in the plasma in a discharge lamp by means of optical methods.

These methods, such as described in H.S. Rothwell, Jr. et al J. IES Oct. 1980, pp. 40-46 and J. F. Waymouth, Electric Discharge Lamps, First Edition, M.I.T. Press, Cambridge, Mass., 1978, pp. 155 and 160-165 rely on an analysis of the emission spectra produced by operating lamps. These methods suffer from the defects of being undesirably slow and of being based on an assumption (among others) that the plasma in the operating lamp is axially symmetric. However, this assumption is not correct when the lamp is operated in a horizontal position.

In addition, by use of optical means it is not possible to obtain the temperature of the plasma near the wall of the plasma-containing tube but only in the luminous region of the arc.

BRIEF SUMMARY OF THE INVENTION

An object of the invention is to provide an improved method for determining the density distribution of species in a plasma. This and other objects of this invention will be apparent from the description that follows.

According to the invention a new and novel method of determining the density distribution in a plasma comprises scanning a cross section of the plasma with an X-ray computerized tomographic scanner (CAT scanner) to determine the attenuation of x-radiation along a plurality of lines in the scanned section of the plasma and generating and recording a series of transmitted intensity values. Such values can be obtained at different angular displacements of the X-ray beam relative to the plasma. By use of tomographic reconstruction algorithms it is possible to transform the values so obtained into a map of density at points within the scanned cross section.

DETAILED DESCRIPTION OF THE INVENTION

Figure 1:
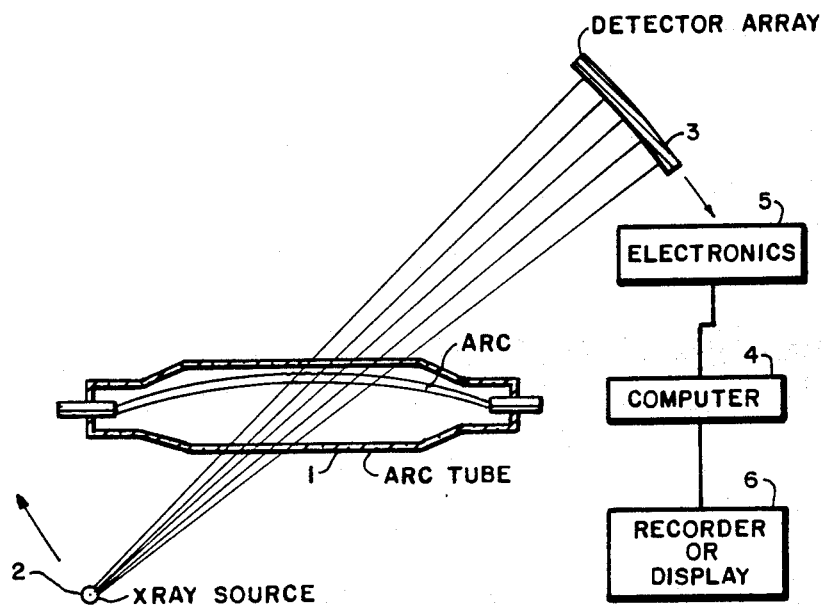
FIG. 1 is a schematic of a horizontally oriented high intensity discharge (HID) lamp positioned in a CAT scanner employed in carrying out the method of the invention.

The use of an absorption of a beam of X-rays passing along the axis of a carbon arc in air to determine the gas density and from that the temperature on the arc axis is described in von Engel and Steinbeck, Siemens-Veroff 10, 155 (1931). Application of this method to an Hg arc is described in Kenty and Karash, Phys. Rev. 60, 66 (1941) and Phys. Rev. 78, 625 (1950). These methods are limited to providing information only of the axial temperature and density and additionally require specifically designed arc tube constructions to perform the measurements.

By employing the CAT scanner according to the method of the invention it is possible to obtain gas density and temperature profiles within a desired cross-sectional area of a plasma and particular of the plasma present in a high pressure discharge lamp. By use of a CAT scanner according to the method of the invention the following two fundamental advantages over the previous attempts to employ X-ray methods for lamp diagnostics are achieved:

1. The method can be applied to ordinary commercial lamps without modification. This is important because one cannot modify the geometry of such lamps without significantly affecting their operating characteristics.

2. The method provides a means for directly obtaining spatially localized density and temperature information within the arc tube. This localized information, which is important in the area of lamp diagnostics, cannot be readily obtained by other means.

In carrying out the method of the invention the arc tube of an operating discharge lamp is positioned within the CAT scanner so that the plane of X-rays defined by the CAT scanner coincides with the plane of the lamp in which the density is to be measured. Thus, if the lamp is horizontally positioned and one is interested in measuring the density profile of the cross sectional plane in the middle of the lamp, the CAT scanner is positioned so that a vertical X-ray scan is performed through that plane.

In the case of a high pressure Hg lamp, the X-ray intensity measured by each detector of the CAT scanner will be $$I_T = I_o \exp\left(-\int_1 \alpha(x, y, z) dl\right)$$

where $I_o$ is the initial intensity of the X-ray beam, $I_T$ is the intensity at the detector, 1 is the path length of the X-ray beam, $\alpha(x,y,z)$ is the absorption coefficient at position $(x,y,z)$ and the integration is performed along the path of the X-ray beam. For atomic or molecular absorption $\alpha(x,y,z) = n(x,y,z)\sigma(E)$, where $\sigma(E)$ is the absorption cross-section for that species at an X-ray energy E and $n(x,y,z)$ is the corresponding species density. As is seen, under fixed experimental conditions, the absorption coefficient is directly related to the species density being measured. In the case of a high pressure Hg lamp the dominant gas phase species during the operation of the lamp is Hg and the small amount of the inert gas present to initiate the discharge does not contribute in any significant extent to the X-ray absorption compared with that contributed to by the Hg.

In the method of the invention data consisting of transmitted X-ray intensity measurements along many different lines within a desired plane in the lamp and measured by an array of detector elements of the CAT scanner is fed into a computer portion of the CAT scanner where a reconstruction algorithm appropriate to the scan geometry is employed to generate a series of density values each value corresponding to a point in the scanned section of the lamp. The generated series of density values is fed to a display portion for example a cathode ray tube where an image consisting of a matrix of pixels to each of which is ascribed a numerical value corresponding to the absorption coefficient of the X-ray image at a particular point and thereby the gas phase density of a point in the tube associated with the pixel.

By this method a qualitative density scale of a cross-section of the plasma in the tube is obtained.

The numerical values obtained can be absolutely calibrated to known densities by repeating the measurements with a Hg filled vessel containing an excess of mercury and heated to a known temperature. Under these conditions the vapor pressure is determined by the temperature of the liquid and the temperature can readily be measured. By measuring the gas volume of the vessel and by use of the gas laws the density can readily calculated. In this manner each pixel value can be associated with an absolute value of mercury density.

Upon obtaining the density profile, the spatially resolved temperature profile $T(x,y,z)$ can be obtained by the use of the gas law: $T(x,y,z) = P/kn(x,y,z)$ where P is the pressure within the arc tube of the lamp and k is the Boltzmann constant.

Since the absolute value of the pressure within the tube is not known it is necessary to calibrate the temperature at one point to absolutely determine the temperature within the profile. This is generally done by measuring the arc tube wall temperature with a pyrometer.

The magnitude of the X-ray absorption generally scales as $z^2$, where $z$ is the atomic number of the elements. Thus Hg has as a much higher absorption cross section than Na. As the position of the characteristic absorption edges are different for different elements these edges can be used to discriminate between elements where a number of elements are present in a plasma in which each makes measurable contributions to the absorption, as will be illustrated below.

While the method of the invention is applicable to the measurement of any gas phase plasma species which exhibits sufficient X-ray absorption, as a practical matter it is most useful for measurement of discharge lamps such as high pressure mercury lamps, metal halide lamps and high pressure sodium lamps.

High pressure mercury lamps are filled with mercury and several tens of Torr of a rare-earth starting gas. Generally only mercury will contribute to the measurable absorption.

Metal halide lamps are filled with mercury and small quantities of a metal halide salts as well as rare-earth starting gases. Again the dominant species is mercury and followed by a much lesser amount of iodine. Since iodine also is a high $z$ element it may contribute to a small but measurable absorption depending upon the sensitivity of the detection and electronics in the CAT scanner used. It is possible to distinguish between mercury and iodine by doing measurements at X-ray energies on either side of a characteristic absorption edge. The species whose absorption edge is bracketed by the two energies will exhibit distinctly different absorption at those energies while the other species will show little change in absorption at the two energies.

The absorption of the species which shows little change in absorption can be subtracted out as a "constant" background, leaving absorption signals which are due only to the one species whose absorption edge occurs between the two measurement energies.

The metal species and the inert starting gas present in the metal halide lamps are too low in atomic number and these species are too low in abundance relative to mercury to contribute to the measured absorption.

High pressure sodium lamps are filled with a small amount of inert starting gas and a mercury/sodium amalgam. Mercury is the most abundant species and the only species to contribute appreciably to the measured absorption. The atomic number of sodium is too low to allow the sodium to contribute appreciably to the measured absorption.

The invention will now be described in greater detail with reference to the drawing, FIG. 1 of which is a schematic of a high pressure arc lamp operating in a horizontal position and positioned in a CAT scanner to provide a scan through a vertical cross-section of the lamp. For this determination the arc tube of a standard 400 W sodium/scandium metal halide discharge lamp 1 was positioned so as to operate horizontally within a commercial CAT scanner comprising an X-ray source 2, a detector array 3 both rotatable along a desired plane of the lamp, a computer 4 for generating a series of density values from the corresponding measurements of attenuation of X-radiation as determined by the detector array 3, interface electronics 5 for electronically conditioning the signal output of the detector array 3 to make it compatible for the computer 4, and a recorder 6 for recording this series of density values comprising a cathode ray tube (not shown) for recording and displaying an image corresponding to the series of density values.

For measuring the density of the plasma in the lamp during operation the arc tube was removed from the outer envelope and the current return wire was removed and rerouted so as to be outside of the X-ray beam. This was done so that the only object intersecting the X-ray beam was the arc tube itself. This was carried out to avoid possible image artifacts from being produced by the reconstruction algorithm.

The arc tube 1 was oriented horizontally within the CAT scanner thus allowing vertical sections to be studied. The peak energy in the X-ray pulse was set at 100 kev, corresponding to an average energy of 50–60 kev.

Figure 2:
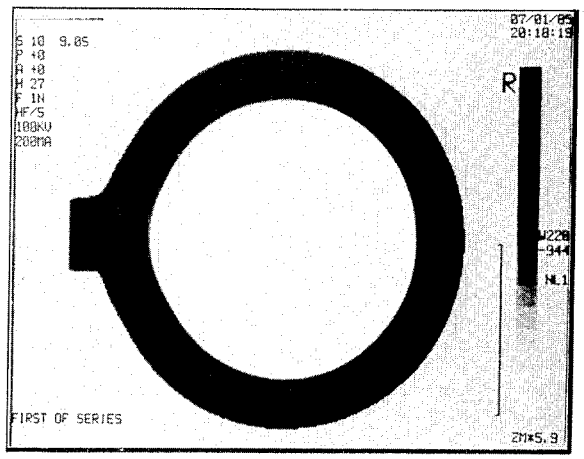
FIGS. 2, 3 and 4 are photographs of reconstructed images obtained from a display of the CAT scanner during various stages of operation of the HID lamp.

FIG. 2 shows a photograph of the screen image on the cathode ray tube screen of the recorder 6 of a vertical section taken through the arc tube when the arc tube is cold. Here the only species in the gas phase is a small amount of argon gas (35 Torr) present to initiate the discharge. This quantity of gas does not contribute to any appreciable X-ray absorption. It should be noted that in this figure no X-ray absorption at all is recorded.

Figure 3:
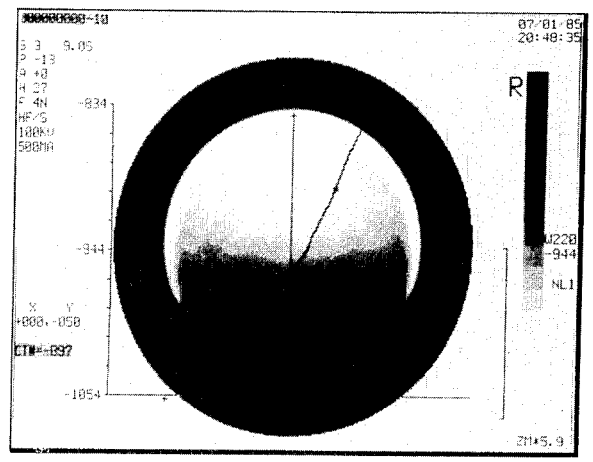

FIG. 3 is a photograph of the screen image for the same vertical section after the discharge has been turned on and the arc tube has been allowed to come to the equilibrium operating condition. At this point the mercury fill in the tube is fully vaporized. As will be noted there is a variation in the degree of greyness of the image which variation corresponds to the amount of gas phase absorption, the darker the area the greater the degree of gas phase absorption. The absorption is asymmetrical as is indicated by the fact that the image is darker in the lower part of the arc tube. This is due to the fact that there is more mercury in the lower part of the arc tube than in the upper part due to convection effects.

Figure 4:
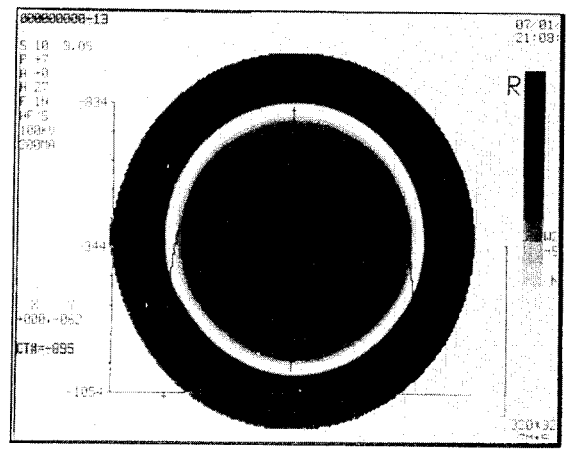

FIG. 4 is a photograph of an image of the scan taken immediately after power to the arc tube was removed. At this point the tube is hot, the arc is extinguished, the temperature gradient produced by the arc has rapidly dissipated and the density distribution is at a relatively uniform value throughout the volume. This shown by the almost uniform nature of the image within the tube. In these photographs a greyness scale R is present to the right of the image.

Besides being displayed on a cathode ray tube screen the image may be photographically recorded using any of the well known photosensitive materials.

While the present invention has been described with references to particular embodiments thereof, it will be understood that numerous modifications can be made by those skilled in the art without actually departing from the scope of the invention.

I claim:

1. A method of determining the density distribution of a plasma comprising scanning a cross-section of said plasma with an X-ray computerized tomographic scanner to determine the attenuation of X-radiation along a plurality of lines traversing said cross section of said plasma, generating and recording a series of transmitted intensity values, each value corresponding to one of the line scans, and employing a reconstruction algorithm to obtain a map of density values at points within the scan cross-section from the line scan values.

2. The method of claim 1 wherein the density values are visually recorded in an image, the image brightness being a representation of said density values.

3. The method of claim 2 wherein the image is formed on the screen of a cathode ray tube.

4. The method of claim 2 wherein the image is photographically formed.

5. The method of claim 1 wherein plasma is contained in an operating discharge lamp.

6. The method of claim 1 wherein the plasma is contained in an operating high pressure metal vapor discharge lamp.

7. A method of determining the density distribution of a plasma comprising scanning a cross-section of said plasma with an X-ray computerized tomographic scanner.

8. A method of measuring the distribution of mercury present in mercury plasma in an operating high-pressure discharge lamp comprising measuring density of said plasma with an X-ray computerized tomographic scanner.

9. A method of determining the density distribution of mercury present in a mercury plasma present in an operating high-pressure discharge lamp comprising scanning a desired cross-section of said lamp containing said plasma, while in operation, with an X-ray computerized tomographic scanner (CAT) to determine the attenuation of X-ray radiation from said scanner along a plurality of lines traversing said cross-section of said plasma, generating and recording a series of transmitted intensity values, each value corresponding to one of the line scans and employing a reconstruction algorithm to obtain a map of density values at points within said scan cross-section from the line scan values.

10. The method of claim 9 wherein the density values are visually recorded in an image, the image darkness being a function of said density values.

11. The method of claim 10 wherein the image is formed on the screen of a cathode ray tube.

12. The method of claim 10 wherein the image is photographically formed.

* * * * *